United States Patent [19]

Thompson

[11] 4,433,239

[45] Feb. 21, 1984

[54] METHOD AND APPARATUS FOR ON-LINE MONITORING OF BITUMEN CONTENT IN TAR SAND

[75] Inventor: Gordon R. Thompson, Edmonton, Canada

[73] Assignee: Petro-Canada Exploration Inc., Calgary

[21] Appl. No.: 233,992

[22] Filed: Feb. 12, 1981

[51] Int. Cl.³ ............................ G01V 9/04; G01J 3/38
[52] U.S. Cl. ................................ 250/255; 250/339; 250/341
[58] Field of Search ............... 250/339, 340, 253, 255, 250/341; 356/418, 448

[56] References Cited

U.S. PATENT DOCUMENTS

| | | | |
|---|---|---|---|
| 3,517,190 | 6/1970 | Astheimer | 250/341 |
| 3,851,175 | 11/1974 | Dahlin et al. | 250/339 |
| 4,149,804 | 4/1979 | Chew III | 356/416 |
| 4,311,393 | 1/1982 | Bartke | 356/448 |
| 4,337,396 | 6/1982 | Lauer et al. | 250/340 |

FOREIGN PATENT DOCUMENTS 711802 6/1965 Canada .................................. 250/339

Primary Examiner—Alfred E. Smith
Assistant Examiner—Carolyn E. Fields
Attorney, Agent, or Firm—E. P. Johnson

[57] ABSTRACT

An improvement in the processing of bituminous sands is described, whereby the concentration of bitumen in tar sand feed is measured by infrared light reflected from the tar sand surface. Near infrared is shone onto the surface of the incoming tar sand and reflected light is collected and passed through two parallel filters, one being a measuring filter having a wavelength range of 2180 to 2260 nm and the other being a reference filter having a wavelength range of 2270 to 2350 nm. The beams emerging from the filters are measured electronically and the resulting signals are separately integrated and amplified by electronic means. The ratio of the amplified signals is used to provide a read-out signal responsive to the bitumen concentration. The results may be used to adjust processing conditions in the extraction process to allow for the variations of bitumen in the feed.

2 Claims, 3 Drawing Figures

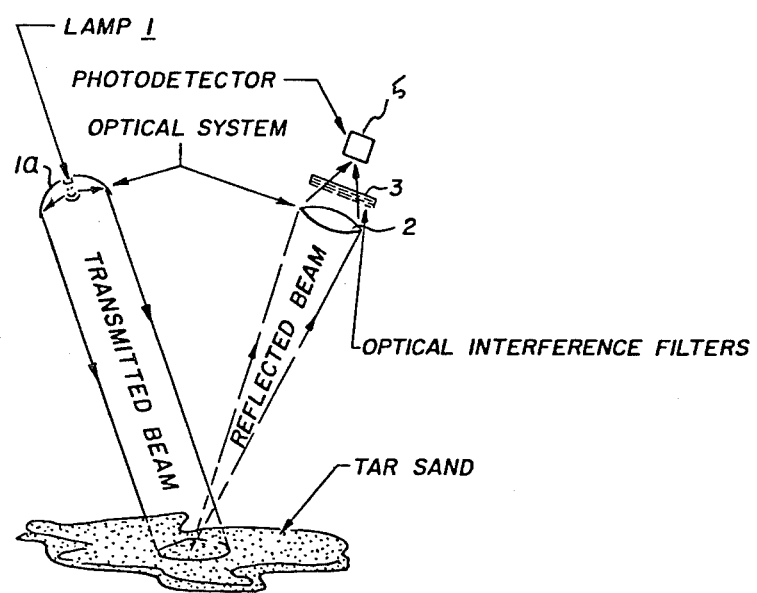

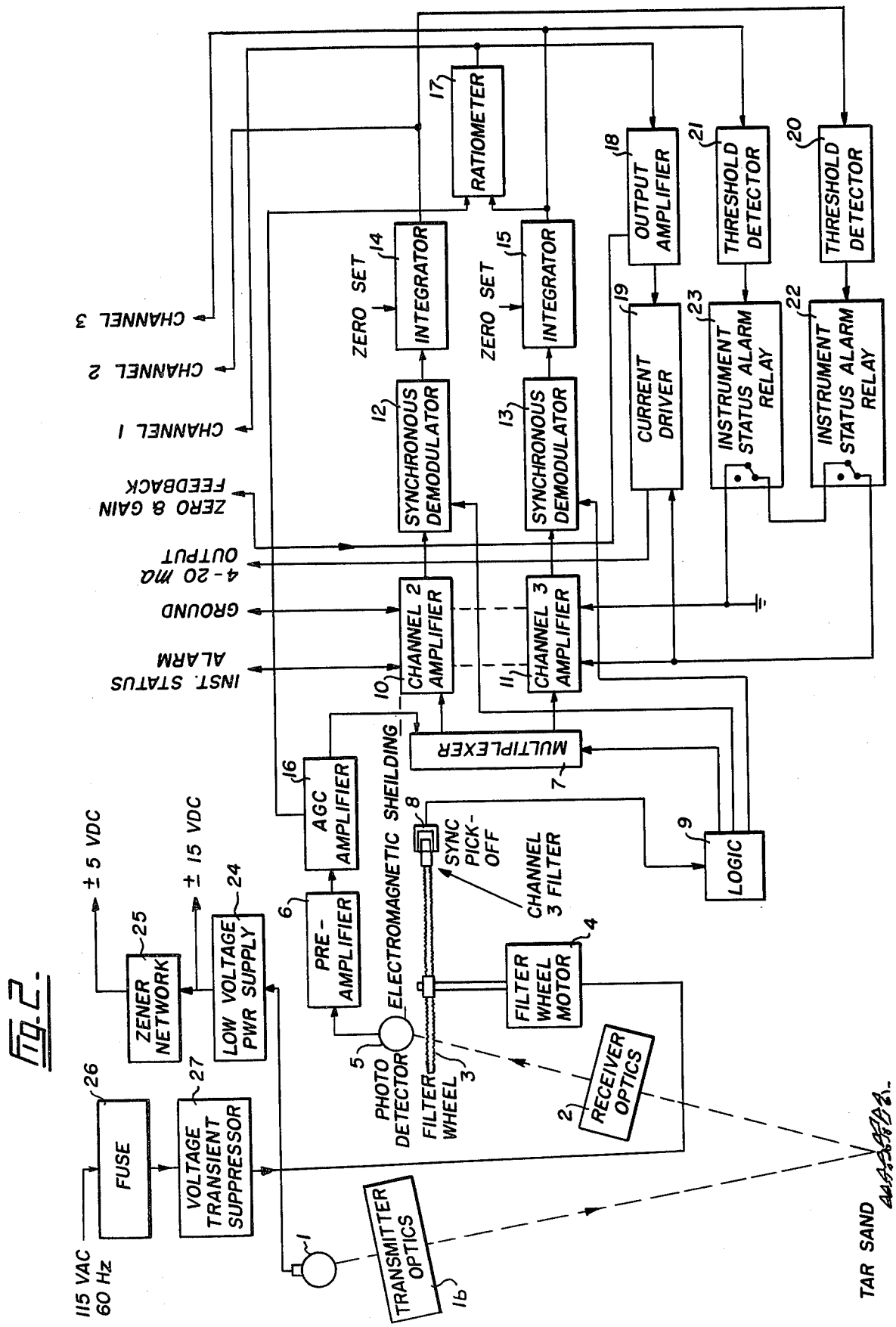

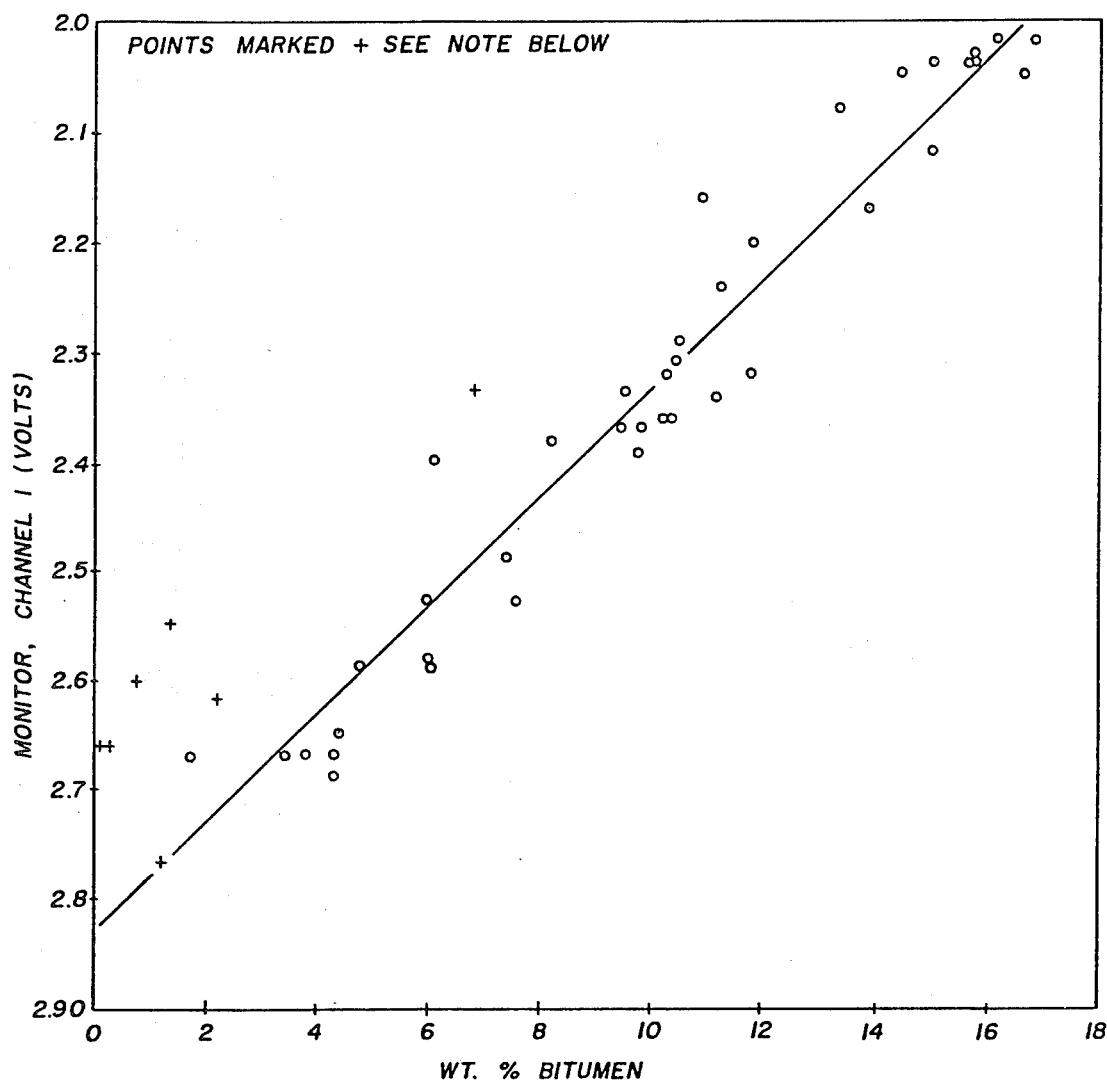

METHOD AND APPARATUS FOR ON-LINE MONITORING OF BITUMEN CONTENT IN TAR SAND

FIELD OF THE INVENTION

This invention relates to an infrared reflectance monitor for indicating the bitumen content trend in tar sand feed.

BACKGROUND OF THE INVENTION

Bitumen is today being commercially extracted from tar sand using a recovery process commonly known as the hot water process.

In general, this process involves: mixing the mined tar sand with hot water, steam and sodium hydroxide in a tumbler; diluting the produced slurry with additional hot water; retaining the diluted slurry under quiescent conditions in an open-topped primary separation vessel having an outlet in its conical base, whereby aerated bitumen rises to form a primary froth, which is collected, and solids settle and are removed through the outlet; withdrawing a dragstream from the middle of the vessel, said dragstream containing non-rising bitumen and clay particles; and subjecting said dragstream to induced air flotation to recover a secondary froth.

The tar sand is a complex material. More particularly, it comprises: sand-size solid grains; connate water sheathing the grains; fine clay-like solids (−325 mesh) which appear appear to be concentrated in the water; and bitumen filling the interstices between the water-sheathed sand grains.

The concentrations of these various components, which make up the tar sand, vary throughout the deposit and hence in the feed led to the extraction plant. These variations in concentration have a marked effect on the efficiency of the recovery process.

The component whose concentration variations can most deleteriously affect the hot water process is the fine solids (hereinafter termed "fines"). The solids component of a low fines tar sand may contain in the order of 5% by weight fines, while the solids component of a high fines tar sand may contain in the order of 20% by weight fines.

Operators of the process can react to the presence of higher levels of fines in the feed by increasing the sodium hydroxide and water additions to the process; these increases will reduce the deleterious effects of the high fines on the efficiency of the bitumen recovery process.

To date, the practice used for monitoring the tar sand composition has involved sampling the feed and subjecting the samples to laboratory analysis. However, this is a time-consuming process and thus the implementation of changes in water and sodium hydroxide addition is late, with the result that the hot water process is rarely operated at optimum conditions.

There has thus existed a long-standing need for an on-line analysing means which would monitor and indicate tar sand feed grade trends accurately and quickly.

It needs to be noted that there is an inverse proportional relationship between bitumen and fines concentrations in tar sand. Therefore the development of an accurate indicator of bitumen content would provide the industry with a means for monitoring fines content.

SUMMARY OF THE INVENTION

In accordance with the invention, tar sand feed grade trends are monitored by:
(a) shining near infrared radiation onto the surface of advancing tar sand;
(b) filtering a first portion of reflected radiation through a first filter which is adapted to pass only radiation of a wavelength range absorbed to a significant extent by bitumen alone among the components of tar sand;
(c) filtering a second portion of reflected radiation through a second filter which is adapted to pass only radiation not absorbed to a significant extent by any component of the tar sand and which has a wavelength close to the first wavelength range;
(d) sensing the radiation passed by the first filter and producing an electrical signal indicative of its intensity;
(e) sensing the radiation passed by the second filter and producing an electrical signal indicative of its intensity;
(f) establishing a ratio of said signals and producing an electrical output indicative of said ratio and which is indicative of the bitumen content of the tar sand;
(g) continuing the foregoing steps sufficiently frequently to give a reading representative of the bitumen content of the tar sand.

In a preferred embodiment of the invention, the first filter is adapted to pass only radiation having a wavelength of about 2180 to about 2260 nm and the second filter is adapted to pass only radiation having a wavelength of about 2270 to about 2350 nm.

It is necessary to have two filters, adapted to pass different wavelengths (a measure and a reference), due to variations in intensity of the incident radiation and to variations in the nature of the reflective surface. Incident radiation can be affected by extraneous sources of light, alterations in electrical supply to the near infrared lamps, or deterioration of those lamps. At the same time, the tar sand reflective surface may vary according to its roughness or smoothness, the quantity of bitumen, or such properties as dryness and degree of oxidation. Before absorption of the near infrared due to bitumen can be determined, it is necessary to compensate for the extent to which the reflected rays are affected by the other properties of the tar sand or the incident radiation. It is thus the purpose of the reference filter to determine those effects on the reflected radiation due to variations of tar sand or incident radiation which are distinct from absorption by bitumen. With this compensating means present, absorption due to bitumen alone is successfully isolated from ancillary variations in reflected radiation. The wavelength range of the reference filter should be close to that of the measure filter, because the extent to which ancillary variations affect reflectance is wavelength-dependent.

The development of the present invention involved some surprising discoveries. Previous uses of reflexive infrared in connection with oil monitoring had been limited to recording oil layers having a thickness in the order of $10\mu$. This is the thickness of, for instance, oil spills on bodies of water. However, penetration to this order of depth would not be useful in tar sand monitoring, as the individual sand particles are commonly thicker than $10\mu$. It follows that one would question whether the infrared would reach interior bitumen. Surprisingly, the infrared appears to penetrate between 1 and 3 mm. into the tar sand. Also, tar sand contains variations in concentration of bitumen and there was concern that these localized rich and lean zones would deleteriously affect the desired performance of the instrument. It was found that manageable absorptions were obtained in both low and high bitumen content zones. Finally, the bituminous component, at the surface of the tar sand mass (such as a layer of tar sand on a conveyor belt), quickly becomes dry and oxidized. Its chemical nature changes significantly from the bitumen present further into the layer. There was therefore concern that this surface effect would affect the reliability of the measurement. However, bitumen readings taken at the surface of a pile have been found to be essentially the same as those obtained after the surface layer is removed.

In addition, the present inventor had to conduct extensive experimentation involving over 130 spectra and many analyses to discover the proper wavelength requirements of the filters.

Broadly stated, the invention is a method for monitoring the bitumen content trends of a layer of tar sand being advanced by a conveyor, comprising: shining an uninterrupted beam of near infrared radiation onto the surface of said advancing tar sand to produce reflected radiation; filtering a first portion of the reflected radiation through a first filter which is adapted to pass only radiation of a wavelength absorbed to a significant extent by bitumen alone among the components of tar sand; filtering a second portion of reflected radiation through a second filter which is adapted to pass only radiation not absorbed to a significant extent by any component of the tar sand and which has a wavelength close to the first wavelength range; sensing the radiation passed by the first filter and producing an electrical signal indicate of its intensity; sensing the radiation passed by the second filter and producing an electrical signal indicative of its intensity; establishing a ratio of said signals and producing an electrical output indicative of said ratio, and which is indicative of the bitumen content of the tar sand; and continuing the foregoing steps sufficiently frequently to give a reading representative of the bitumen content of the tar sand.

In another aspect of the invention, there is provided an infrared reflectance monitor for indicating the bitumen content trend in a layer of tar sand feed being advanced by a conveyor, said monitor comprising: a source of infrared radiation, which radiation may be directly shone at the tar sand; means for focusing radiation reflected by the tar sand; first and second filters that may be alternately positioned in the path of the focused reflected radiation, the first such filter being adapted to pass only wavelengths of about 2180 to about 2260 nm, absorbed by bitumen alone among the components of the tar sand, the second such filter being adapted to pass only wavelengths of about 2270 to about 2350 nm, not absorbed by any of the tar sand components; and means for sensing the intensity of each passed radiation species and producing a signal indicative of the bitumen content.

DESCRIPTION OF THE DRAWINGS

FIG. 1 is a schematic showing the interrelationship of the principal elements of the instrument up to the photodetector;

FIG. 2 is a schematic showing a known instrument incorporated into the invention;

FIG. 3 is a plot showing a typical relationship between bitumen content in tar sand as determined by reflective infrared and as determined by laboratory analysis.

DESCRIPTION OF THE PREFERRED EMBODIMENT

The present tar sand monitor is an instrument which, when suspended about 40 to 60 inches above the tar sand, provides a remote indication of the bitumen concentration (weight percent) in the surface layer of said tar sand. When the tar sand is on a moving conveyor belt, the instrument continuously produces a measurement which is an averaging of the bitumen content of a strip observed over a period of approximately 30 seconds. The strip typically has a width of approximately 6 inches and a length of approximately 250 feet.

A greatly simplified layout is given in FIG. 1 to show the interrelationship of the optical and electronic elements. For greater detail, refer to FIG. 2. The monitor comprises a source of infrared radiation, more particularly a Tungsten-halogen lamp 1, mounted at the focal point of an aluminum parabolic reflector 1a. The lamp 1 is used in conjunction with a focusing lens 1b. Preferably, dual transmitters (not shown) are used, to ensure continuous operation if one lamp burns out. As stated, the lamp 1 beams radiation at the tar sand surface, which radiation is partly reflected.

A receiver lens 2 is suitably mounted in the path of the reflected radiation. The lens 2 functions to focus the incoming radiation to a small point. An arsenic trisulfide lens is suitable for this purpose.

A filter wheel 3 is positioned between the lens 2 and the latter's focal point. The wheel 3 carries a pair of filters of the following specification:

| Filter No. 1 | |
|---|---|
| center wavelength | 2.22 $\mu$m ± 0.01 $\mu$m |
| half-band width | 0.08 $\mu$m ± 0.11 $\mu$m |
| transmission on wavelength | 50% peak or greater |
| transmission off wavelength | 0.1% absolute or less at all wavelengths out of band to 5 $\mu$m |
| Filter No. 2 | |
| Center wavelength | 2.33 $\mu$m ± 0.02 $\mu$m |
| half-band width | 0.08 $\mu$m ± 0.11 $\mu$m |
| transmission on wavelength | 50% peak or greater |
| transmission off wavelength | 0.1% absolute or less at all wavelengths out of band to 5 $\mu$m |

Filter No. 1 passes only radiation of a wavelength absorbed to a significant extent by bitumen alone among the components of the tar sand. The beam passed by this filter is termed the measure beam. Filter No. 2 passes only radiation of a wavelength not absorbed by any of the components of tar sand; this radiation has a wavelength close to the measuring wavelength. The beam passed by filter No. 2 is termed the reference beam.

The lamp 1, receiver lens 2, filter wheel 3, and most of the electronic equipment shown schematically in FIG. 2 and briefly described below are commercially available from Wright and Wright Inc., Oak Bluffs, Mass., in the form of a monitor designated Model E 250.

Continuing now with such description, a photodetector 5 is provided at the focal point of the receiver lens 2. This photodetector senses each of the alternately passed measure and reference beams and emits electrical signals proportional to their intensities. An indium arsenide photodetector is suitable for this purpose.

With reference now to FIG. 2, the photodetector signals are transmitted to and amplified by a preamplifier 6. The preamplifier output is fed to an AGC amplifier 16 and thence to a multiplexer 7.

A sync pick-off 8 is provided to sense and indicate when each filter is directing a beam at the photodetector 5. This sync pick-off 8 comprises a U-shaped optical switch straddling the filter wheel 3 and employing a light source and a silicon photodetector at opposite ends of the switch. Light emitted by the sync pick-off passes through slots in the outer edge of the filter wheel and thus periodically transmits a signal determined by the filter wheel position.

The pick-off signals are transmitted to a logic circuit 9 which functions to switch the multiplexer 7 to transmit the detected and amplified signal to either the measuring signal amplifier 10 or reference signal amplifier 11, depending on which filter is sensed to be in front of the photodetector 5.

There are provided measure and reference signal processing means comprising amplifiers 10, 11, synchronous demodulators 12, 13 and integrators 14, 15. The multiplexer 7 alternately shorts to ground that amplifier 12 or 13 not passing the detected and amplified signal. The synchronous demodulators 12,13 allow only signals of the frequency corresponding to the rotational speed of the filter wheel to be passed, with other frequencies being rejected. They thus reduce the electronic noise in the signal.

Each amplifier 10, 11 has adjustable gain from approximately $\times 1.0$ to $\times 10.0$, as well as zero adjustment. The amplified measure or reference signals are detected by the synchronous demodulators 12, 13 respectively. The demodulators 12, 13 are operative to pass signals at exactly the same frequency as the chopped frequency of light detected by the photodetector 5. The chopped frequency is of course set by the rotational frequency of the filter wheel 3. The sync pick-off 8 senses this chopped frequency and feeds this frequency to each of the synchronous demodulators 12, 13 through the logic circuit 9. The demodulators 12, 13 reject all detected analog signals other than this chopped frequency to thereby increase the signal-to-noise ratio.

The detected signals from demodulators 12, 13 are fed to integrators 14, 15 respectively. The integrators 14, 15 average the signal strength over a preset interval of time to compensate for signal variations due to rocks, clay lumps and variations in the tar sand oil content. A 30-second time constant has been found suitable.

An automatic gain control circuit 16 referred to as the AGC amplifier is provided to control the strength of the signals fed to the amplifiers 10, 11. The gain control circuit 16 senses the output voltage from the integrator 14, and if low, increases the gain of the AGC amplifier. Conversely, when the output voltage of the integrator 14 is high, the gain control circuit 16 reduces the gain of the AGC amplifier to prevent saturation of the amplifiers 10, 11.

The averaged signals from the integrators 14, 15 ($v_{integrator\ 14}$ and $v_{integrator\ 15}$) respectively are fed to a ratiometer 17. The ratiometer 17 calculates a voltage output ratio ($v_{out}$) of the two signal strengths according to the equation 1 below:

$$v_{out} = 2.0 \times \frac{v_{integrator\ 15}}{v_{integrator\ 14}} \text{ Volts} \qquad (1)$$

The ratiometer 17 operates with a conventional logrithm, summation, antilog method to obtain the ratio ($v_{out}$).

The output ($v_{out}$) from the ratiometer 17 is fed through an output amplifier 18 and a current driver 19, and finally to an output meter (not shown). The output signal $I_{out}$ is also run to an external potentiometer (not shown) which returns an adjustable feedback signal to the input of the output amplifier 18 to provide current gain control. Also provided externally is a zero control (not shown). The zero and current gain controls allow adjustment such that a standard 4 to 20 mA current signal represents the desired range of bitumen content (5 to 15% bitumen).

The output signals from the integrators 14, 15 are also fed to threshold detectors 20, 21 respectively. Each of the threshold detectors 20, 21 is in turn connected to an instrument status alarm relay 22, 23 respectively. The threshold detector 20, 21 activates when the voltage level of integrator 14 or 15 output approaches zero. Activation causes the contacts of the alarm relay 22 or 23 to open, thereby indicating a monitor malfunction. Further, loss of power to the monitor de-energizes and opens the alarm relays 22,23 to indicate failure. Opening of the relay 22 or 23 forces the current output of the current driver 19 to zero.

The output meter (not shown) is a digital voltmeter which displays the amplified output signal from the current driver 19.

The monitor as described above operates off 115 V AC (60 Hz) line power and thus is provided with a low voltage power supply 24 to convert this power to $\pm 15$ V DC. The $\pm 15$ V DC is further converted to 5 V DC through a zener network 25. The monitor components operate from the 5 V or $\pm 15$ V DC power supply.

The AC input to the monitor is internally fused at 26 to prevent short circuit damage to the monitor. The AC input is also passed through a voltage transient suppressor 27 to suppress high voltage spikes.

FIG. 3 shows that, over the range of bitumen values of interest in various tar sand feeds, there is a linear relationship between the bitumen contents determined by chemical analysis and those determined by the infrared reflectance monitor.

While the present invention has been disclosed in connection with the preferred embodiment thereof, it should be understood that there may be other embodiments which fall within the spirit and scope of the invention as defined by the following claims.

The embodiments of the invention in which an exclusive property or privilege is claimed are defined as follows:

1. A method for monitoring the bitumen content trends of an advancing layer of tar sand, comprising:
   shining an uninterrupted beam of near infrared radiation onto the surface of said advancing tar sand to produce reflected radiation;
   filtering a first portion of the reflected radiation through a first filter which passes only wavelengths of about 2180 to about 2260 nm;
   filtering a second portion of reflected radiation through a second filter which passes only wavelengths of about 2270 to about 2350 nm;

sensing the radiation passed by the first filter and producing an electrical signal indicative of its intensity;

sensing the radiation passed by the second filter and producing an electrical signal indicative of its intensity;

establishing a ratio of said signals and producing an electrical output indicative of said ratio and which is indicative of the bitumen content of the tar sand; and continuing the foregoing steps sufficiently frequently to give a reading representative of the bitumen content of the tar sand.

2. An infrared reflectance monitor, for indicating the bitumen content trend in a layer of tar sand feed being advanced past the monitor, comprising:

means for beaming infrared radiation at the tar sand;

means for focusing radiation reflected by the tar sand;

a first filter for passing only wavelengths of about 2180 to about 2260 nm;

a second filter for passing only wavelengths of about 2270 to about 2350 nm;

means for alternately positioning the filters in the path of the focused reflected radiation; and means for sensing the intensity of each radiation species alternately passed by the filters and producing a signal indicative of the bitumen content.

* * * * *

UNITED STATES PATENT AND TRADEMARK OFFICE
CERTIFICATE OF CORRECTION

PATENT NO. : 4,433,239
DATED : February 21, 1984
INVENTOR(S) : Gordon R. Thompson It is certified that error appears in the above-identified patent and that said Letters Patent is hereby corrected as shown below:

On the title page Item (73) add the following assignees

-- Her Majesty the Queen in right of the province of Alberta

PanCanadian Petroleum Limited

Esso Resources Canada Ltd.

Canada-Cities Service, Ltd.

Gulf Canada Limited

Alberta Energy Company Ltd.

Hudson's Bay Oil and Gas Company Limited

Petrofina Canada Inc. --

Signed and Sealed this

Nineteenth Day of June 1984

[SEAL]

Attest:

*Attesting Officer*

GERALD J. MOSSINGHOFF
*Commissioner of Patents and Trademarks*